United States Patent
Yokoi et al.

(10) Patent No.: US 11,107,214 B2
(45) Date of Patent: Aug. 31, 2021

(54) METHOD AND DEVICE FOR EVALUATING TEAR FLUID LAYER DYNAMICS

(71) Applicants: KYOTO PREFECTURAL PUBLIC UNIVERSITY CORPORATION, Kyoto (JP); KOWA COMPANY, LTD., Aichi (JP)

(72) Inventors: Norihiko Yokoi, Kyoto (JP); Katsumi Yabusaki, Higashimurayama (JP)

(73) Assignees: KYOTO PREFECTURAL PUBLIC UNIVERSITY CORPORATION, Kyoto (JP); KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 16/609,649

(22) PCT Filed: Apr. 27, 2018

(86) PCT No.: PCT/JP2018/017115
§ 371 (c)(1),
(2) Date: Oct. 30, 2019

(87) PCT Pub. No.: WO2018/203515
PCT Pub. Date: Nov. 8, 2018

(65) Prior Publication Data
US 2020/0074627 A1 Mar. 5, 2020

(30) Foreign Application Priority Data
May 1, 2017 (JP) .............................. JP2017-090949

(51) Int. Cl.
*G06K 9/00* (2006.01)
*G06T 7/00* (2017.01)
(Continued)

(52) U.S. Cl.
CPC ............ *G06T 7/0012* (2013.01); *A61B 3/101* (2013.01); *A61B 3/1015* (2013.01);
(Continued)

(58) Field of Classification Search
CPC .................................................. G06T 7/0012
See application file for complete search history.

(56) References Cited

U.S. PATENT DOCUMENTS 6,236,459 B1  5/2001  Negahdaripour et al.
2005/0162611 A1  7/2005  Miwa
(Continued)

FOREIGN PATENT DOCUMENTS

EP  3 466 319 A1  4/2019
JP  H09-201334 A  8/1997
(Continued)

OTHER PUBLICATIONS

Shunji Nakao, "Dry Eye Diagnosis PPP (Preferred Pattern of Practice)," May 1, 2002, Dry Eye Society, Medical View Co., Ltd., pp. 41-45; with machine translation.
(Continued)

*Primary Examiner* — Oneal R Mistry
(74) *Attorney, Agent, or Firm* — McDermott Will and Emery LLP

(57) ABSTRACT

A method and device for evaluating the dynamics of a tear fluid layer to objectively and accurately evaluate breakdown of the tear fluid layer, which is a core mechanism of dry eye, are provided. The method includes a step of acquiring color information of each pixel in a predetermined region of a tear fluid layer interference fringe image, which is a moving image or a plurality of static images, a step of calculating a numerical value indicating the diversity of color from the acquired color information, a step of calculating the average value of the color information, and a step of calculating a
(Continued)

coefficient of variation on the basis of the calculated numerical value indicating the diversity of color and the calculated average value of the color information. The coefficient of variation is used as an index for evaluating the dynamics of the tear fluid layer.

14 Claims, 2 Drawing Sheets

(51) Int. Cl.
*G06T 7/90* (2017.01)
*A61B 3/10* (2006.01)
*A61B 5/103* (2006.01)

(52) U.S. Cl.
CPC .............. *A61B 5/1032* (2013.01); *G06T 7/90* (2017.01); *G06T 2207/30041* (2013.01)

(56) References Cited

U.S. PATENT DOCUMENTS

| | | | |
|---|---|---|---|
| 2010/0253907 A1* | 10/2010 | Korb | A61B 3/101 351/206 |
| 2012/0300174 A1 | 11/2012 | Yokoi et al. | |
| 2015/0138505 A1* | 5/2015 | Grenon | A61B 3/0008 351/206 |
| 2015/0141278 A1* | 5/2015 | Hollman-Hewgley | G06T 7/0012 506/9 |
| 2017/0236259 A1* | 8/2017 | Park | G06T 5/006 382/167 |
| 2020/0315446 A1 | 10/2020 | Yabusaki | |

FOREIGN PATENT DOCUMENTS

| | | |
|---|---|---|
| JP | 2005-211173 A | 8/2005 |
| JP | 2011-156030 A | 8/2011 |
| WO | 2015/073664 A2 | 5/2015 |
| WO | 2017/209024 A1 | 12/2017 |

OTHER PUBLICATIONS

International Search Report and Written Opinion issued in International Patent Application No. PCT/JP2018/017115, dated May 29, 2018; with partial English translation.

Extended European Search Report issued in European Patent Application No. 18794052.3, dated Dec. 10, 2020.

* cited by examiner

[Fig.1]
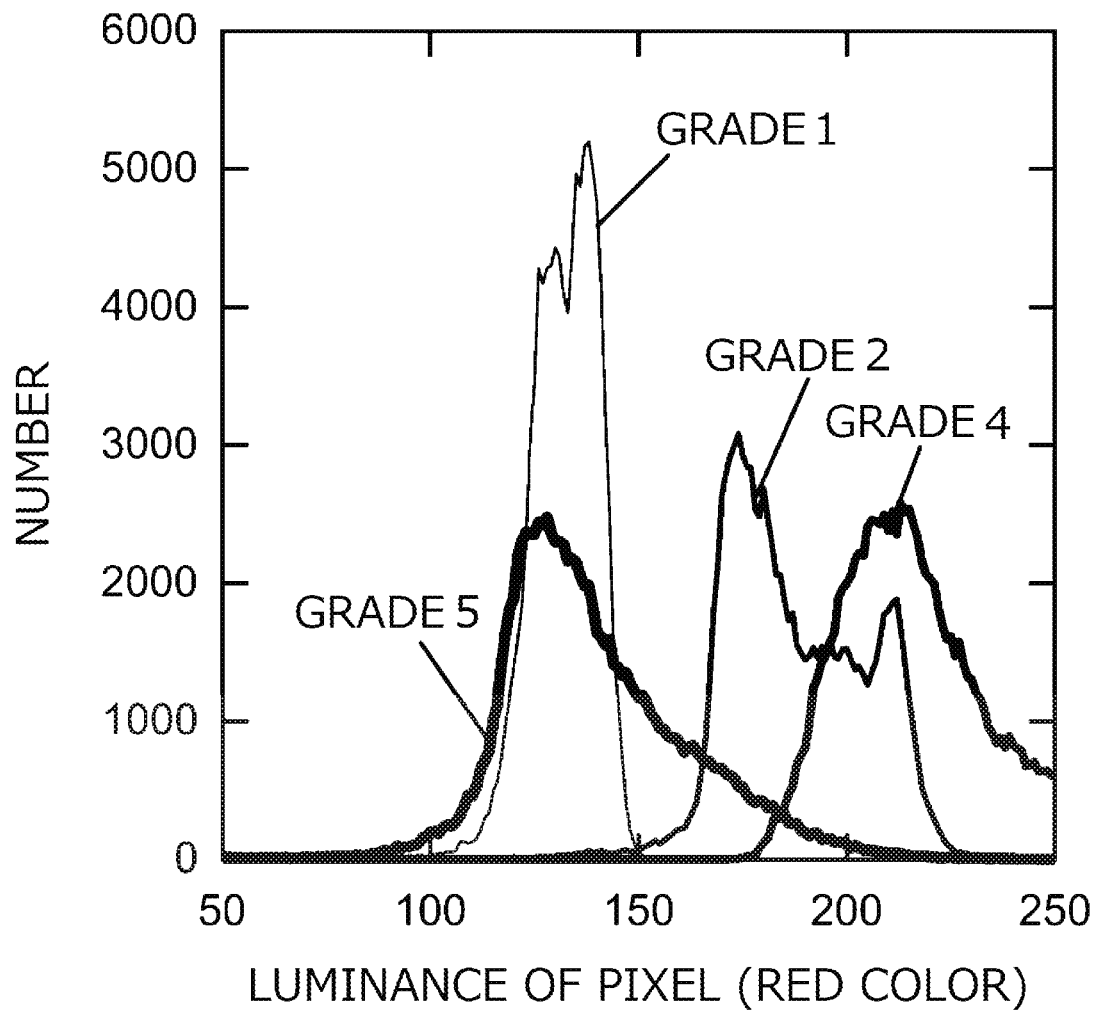
[Fig.2]
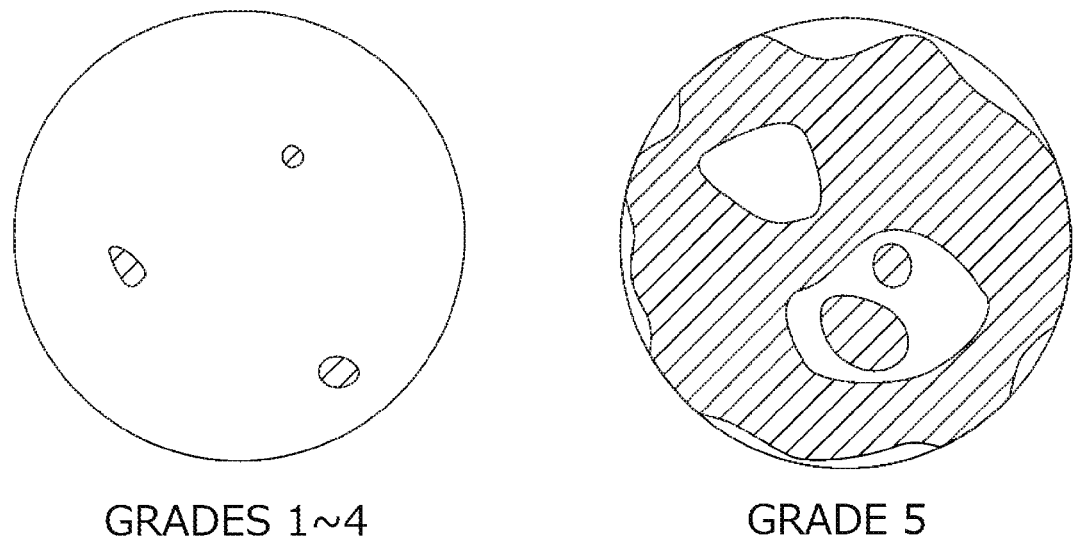
GRADES 1~4          GRADE 5

[Fig.3]
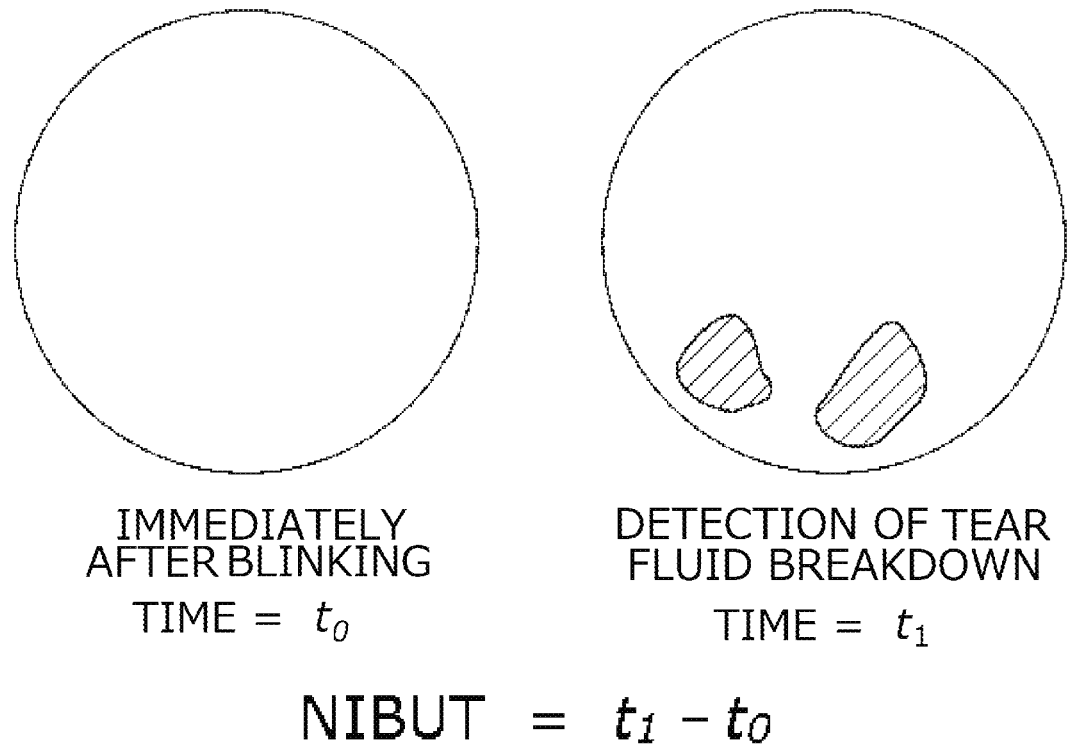
IMMEDIATELY AFTER BLINKING
TIME = $t_0$
DETECTION OF TEAR FLUID BREAKDOWN
TIME = $t_1$
NIBUT = $t_1 - t_0$
[Fig.4]
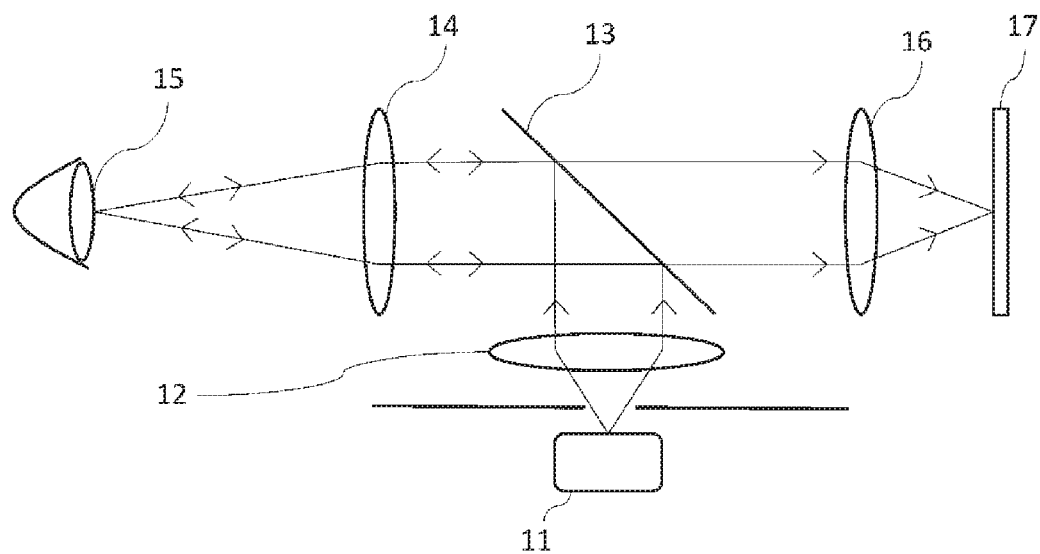

METHOD AND DEVICE FOR EVALUATING TEAR FLUID LAYER DYNAMICS

CROSS-REFERENCE OF RELATED APPLICATIONS

This application is the U.S. National Phase under 35 U.S.C. § 371 of International Patent Application No. PCT/JP2018/017115, filed on Apr. 27, 2018, which in turn claims the benefit of Japanese Application No. 2017-090949, filed on May 1, 2017, the entire disclosures of which Applications are incorporated by reference herein.

FIELD

The present invention relates to a method and device for evaluating the dynamics of a tear fluid layer by using the diversity of color of an interference fringe generated by an oil layer of a tear fluid.

BACKGROUND

An eyeball and an eyelid are protected by a tear fluid from entry of a foreign matter, drying, damages due to friction, and the like. The tear fluid forms a tear fluid layer composed of two layers, a liquid layer including water that occupies most of the tear fluid, a glycoprotein (mucin) and a protein, and an oil layer covering the liquid layer. The oil layer prevents evaporation of a water content of the liquid layer by preventing the liquid layer from being in direct contact with the air. The components of the oil layer are secreted from the meibomian gland present in the eyelid. If the meibomian gland is damaged due to aging, inflammation, scratching, or the like, the oil layer is not properly formed, causing an eye-surface condition of so-called dry eye. Thus, evaluating the oil layer of the tear fluid layer is effective in diagnosing the severity of the dry eye.

In this context, a device for diagnosing five levels (grades) of the severity of the dry eye by photographing an interference fringe formed on the oil layer and visually inspecting the state of the oil layer have been proposed heretofore (Patent literature 1 and Patent literature 2). The interference fringe of the tear fluid layer is basically the same as that observed in a soap bubble, a thin oil film formed on a water surface, or the like. However, in the case of the tear fluid layer, the interference fringe is formed by interference between light reflected on the surface of the oil layer and light reflected at a boundary of a lower surface of the oil layer and the liquid layer.

If the oil layer formed on the liquid layer is stable and uniform in thickness, an image of the tear fluid appears gray in monotone without interference of light occurring (grade 1). As the thickness of the liquid layer becomes thin, that is, as the water amount of the tear fluid decreases, the thickness of the oil layer becomes thick and a length of light wavelength satisfy a condition where the interference occurs, so that the interference fringe begins to appear. At the beginning, the interference fringes of different gray colors appear (grade 2), however, when the thickness of the oil layer becomes uneven, the interference fringes of various colors appear (grade 3). When the thickness of the oil layer becomes further uneven, these interference fringes of various colors are jumbled and mixed (grade 4).

In particular, in Sjögren's syndrome in which the tear glands that secret the tear fluid are damaged by abnormal immunity, or the like, a level of the tear fluid is significantly reduced and the cornea and the conjunctiva are not protected by the tear fluid even by blinking, thereby causing severe dry eye. In such a case, an interference fringe image of the tear fluid layer appears dark as a whole and also noticeably rough due to a large disturbance in the oil layer, resulting in a diagnosis of grade 5. Further, a condition of the interference fringe of the tear fluid layer of grade 5 is similar to that of the interference fringe of the broken tear fluid layer. This is because the tear fluid layer of grade 5 is broken down immediately after blinking.

CITATION LIST

Patent Literature

Patent Literature 1: Japanese Patent Application Laid-Open No. Hei, 9-201334
Patent Literature 2: Japanese Patent Application Laid-Open No. 2011-156030
Patent Literature 3: Japanese Patent Application No. 2016-107338

Non-Patent Literature

Non-Patent Literature 1: "Dry Eye Diagnosis PPP (pp. 41 to 45)" (first edition, first printing: May 1, 2002, Edited by: Dry Eye Society, Publisher: Shuhji Nakao, Publishing Office: Medical View Co., Ltd.)

SUMMARY

Technical Problem

However, determining the grade of the dry eye by visual inspection in this manner requires an experienced skill for achieving an accurate diagnosis. Further, even an experienced observer reveals an inconsistency in determining a diagnosis result due to prejudice or misunderstanding, and a determination result is varied from observer to observer due to individual subjectivity, which have been problems with this method. Thus, there has been desired a method in which the state of the oil layer of a tear fluid layer can be automatically digitized in the similar manner as the grade determination by visual inspection.

In automatically determining the grade, a color state of the interference fringe of the tear fluid layer unidirectionally changes from a dark monotone to bright rainbow colors until grade 4, that is, there is a correlation between the grade and the color state of the interference fringe, and thus the grade can be determined by the color state of the interference fringe using a method described in Patent Literature 3. However, in automatically determining grade 5, the color state of the interference fringe appears dark with rough feeling, making grade 5 not being on an extension of the correlation until grade 4. As a result, it is necessary to diagnose grade 5 in combination with another index different from the one used for determining grade 4 or earlier, making the grade determination complicated.

Further, although a tear fluid layer image can be obtained as a video image consisting of sequential images, diagnosis of the state of the tear fluid layer by visual inspection does not allow a temporal and spatial analysis, thus making it hard to dynamically analyze information included in measurement data, such as fluidity and a state change of the tear fluid layer.

As shown in Non-Patent Literature 1, in particular, measuring a time until the breakdown of the tear fluid layer (BUT: Break Up Time) makes it possible to evaluate the stability of the tear fluid layer and serves as an important item for diagnosing the severity of dry eye. The time until the breakdown of the tear fluid layer has been conventionally acquired by visual inspection using a stopwatch or the like. However, it has been difficult to determine at what time point the tear fluid layer is broken down, making it difficult to exclude observer bias. Thus, a method for automatically measuring BUT has been desired.

The present invention has been made in view of the conventional problems described above and an object of the present invention is to provide a method for diagnosing a patient with high severity represented by grade 5, in which a color variation in a tear fluid layer interference fringe image is evaluated as a coefficient of variation to detect a site where the tear fluid layer is broken down and the diagnosis is performed on the basis of a lapse of time after blinking and a ratio of a site of the breakdown with respect to the entire image, a method for noninvasively measuring a time until the breakdown of the tear fluid layer (BUT) by evaluating the variation as the coefficient of variation (NIBUT: Non-Invasive Break Up Time), and a method and device for evaluating the dynamics of the tear fluid layer used for diagnosing a causes of dry eye by evaluating the variation as the coefficient of variation.

Solution to Problem

The method and device for evaluating the dynamics of the tear fluid layer according to the present invention include the following steps or means.
(1) The method and device include a step of acquiring color information of each pixel in a predetermined region of a tear fluid layer interference fringe image, which is a moving image or a plurality of static images, a step of calculating a numerical value indicating a diversity of color from the acquired color information, a step of calculating an average value of the color information, and a step of calculating a coefficient of variation on the basis of the calculated numerical value indicating the diversity of color and the calculated average value of the color information. Herein, the coefficient of variation is used as an index for evaluating the dynamics of the tear fluid layer.
(2) in the (1) described above, the color information is luminance or brightness of the pixel, and the numerical value indicating the diversity of color is a variation of the luminance or the brightness.
(3) In the (2) described above, the variation of the luminance or the brightness is a standard deviation of the luminance or the brightness.
(4) In the (1) to (3) described above, the coefficient of variation is a numerical value obtained by dividing the numerical value indicating the diversity of color information by the average value of the color information.
(5) In the (1) to (4) described above, a step of calculating a region area of a region indicated by the coefficient of variation exceeding a threshold value and a determination step of determining whether the region area exceeds a threshold value are included.
(6) In the (5) described above, a step of acquiring a predetermined start time, a step of acquiring a time when the region area exceeds the threshold value by the determination step as an end time, and a step of calculating a time from the start time to the end time are included.
(7) In the (1) to (6) described above, the coefficient of variation is used as an index for evaluating grade 5 in severity of dry eye.
(8) in the (1) to (6) described above, the numerical value indicating the diversity of color or the coefficient of variation is used as an index for evaluating grades 1 to 4 in the severity of dry eye.

Advantageous Effects of Invention

The present invention exhibits the following advantageous effects. A state of the interference fringe of the tear fluid layer can be digitized by determining the diversity of color in a region of the image of interest on the basis of the color information of a pixel included in such a region, and the numerical value indicating the diversity of color can be used as an index for evaluating the state of the tear fluid layer. This makes it possible to objectively evaluate the state of the tear fluid layer, in particular, a degree to which the tear fluid layer is broken down without depending on subjectivity, experience, or the like of an observer.

Further, a planar (or spatial) distribution of the state of a tear fluid layer can be evaluated by dividing the tear fluid layer interference fringe image into a number of regions and calculating the numerical value representing the diversity of color in each region, or by specifying each pixel or a small group of pixels and calculating the numerical value representing the diversity of color in a region surrounding each pixel or the small group of pixels. This makes it possible to easily and objectively determine a site in which the state of a tear fluid layer deteriorates on the cornea.

Further, in the case of a moving image, a temporal transition of the state of the tear fluid layer can be analyzed and evaluated by retrieving and analyzing two or more frames of the moving image. This makes it possible to automatically calculate a time from blinking to the breakdown of the tear fluid layer (NIBUT).

BRIEF DESCRIPTION OF DRAWINGS

FIG. 1 is a diagram illustrating a luminance histogram of a red color element extracted from RGB color space elements of a tear fluid layer interference fringe image of each grade.

FIG. 2 is a schematic diagram illustrating a relation between severity of dry eye and an acquired image, in which a diversity of color of a tear fluid interference fringe is obtained as a coefficient of variation by dividing a standard deviation of luminance of a color element by an average value of the luminance. A shaded portion in the figure indicates a site where the coefficient of variation of the luminance shows a high value in the tear fluid layer interference fringe image according to the present invention, that is, a site where the teal fluid layer is broken down or a cornea surface is exposed.

FIG. 3 is a schematic diagram illustrating a method for determining a time until the breakdown of the tear fluid layer, that is, BUT, by determining the diversity of color of the interference fringe of the tear fluid layer as the coefficient of variation of the luminance. Similar to FIG. 2, a shaded port on indicates a site where the tear fluid layer is broken down or a cornea surface is exposed.

FIG. 4 is a schematic view illustrating a configuration of a tear fluid layer interference fringe image acquiring device.

DESCRIPTION OF EMBODIMENTS

Hereinafter, embodiments of the present invention will be described by way of examples. In the present invention, color information of all or a part of pixels in an entire region of an image or at least one or more regions arranged in the image is acquired and a diversity of color of at least two or more of the pixels is calculated to determine a degree of breakdown of a tear fluid layer and a site of the breakdown on the basis of the diversity of color of an interference fringe of the tear fluid layer shown in such a region.

<Image Acquisition>

As a device for acquiring the tear fluid layer image on the surface of an eye (a tear fluid layer interference fringe image acquisition device), a conventionally known device may be appropriately used as long as it can record the photographed image showing the interference fringe of the tear fluid layer as digital data. For example, in the tear fluid layer interference fringe image acquisition device schematically shown in FIG. 4, a light beam, which has been emitted from a light source 11 and transmitted through a diaphragm, sequentially passes through a lens 12, a splitter 13, and an objective lens 14 and is condensed on an anterior eye portion 15 of a subject eye of a subject. Reflected light from the anterior eye portion 15 passes through the objective lens 14 and the splitter 13, so that an image is formed on an imaging element 17 via an imaging lens 16. Photographed data of the image formed on the imaging element 17 are subjected to a predetermined processing by an image processing engine and converted to image data and moving image data.

The tear fluid layer interference fringe image acquisition device is physically or logically connected to a dynamics evaluation device of a tear fluid layer according to the present invention. The dynamics evaluation device of a tear fluid layer includes a processing unit configured to compute and process data and a storing unit configured to store the image data, moving image data, and other data acquired by the tear fluid layer interference fringe image acquisition device. The storing unit stores a computer program and prescribed data for implementing the present invention, while the processing unit processes data according to a predetermined instruction by the computer program and the like.

<Acquisition of Image Color Information>

A specific processing of the dynamics evaluation device of a tear fluid layer will be described below. The color information is acquired from the image data of the interference fringe of the tear fluid layer (a tear fluid layer interference fringe image) obtained as described above and a diversity of color is calculated to obtain an index for evaluating the state of the tear fluid layer. A description will next be given of a method of using color elements of three colors of red, green and blue (a numerical value in the RUB color space), which is a color system used in many electronic image apparatuses as the color information to be used in the present invention.

Specifically, the color information of each pixel is luminance or brightness of color elements of red, green, and blue possessed by a pixel, and, as the color information of each pixel, luminance of at least one or more color elements of red, green, and blue in the RGB color space may be directly used or a secondary numerical value calculated from the color information may be obtained and used. For example, as a method for creating a gray scale suitable for human color perception, a calculation method in which the luminance of each of red, green, and blue is multiplied by a corresponding predetermined coefficient (for example, red "0.298912", green "0.586611", blue "0.114478") and then the resulting values are summed up is known. As exemplified above, the color information may be processed into gray scale gradation by a predetermined method and used.

Further, the luminance of any of the color elements may be used solely or two or more thereof may be used in combination for the calculation. For example, in the case of using an average value, two or more of the color elements may be simply averaged to perform a calculation or each element may be multiplied by a different predetermined weighting coefficient to calculate an average value.

Alternatively, the coefficient of variation may be individually calculated from three color elements of red, green, and blue, and, for example, the maximum value, the minimum value, or the second largest numerical value among them may be used.

The above-described method is the method for acquiring the color information of the image using a numerical value in the RGB color space. However, as the color information used in the present invention, luminance or brightness defined by the HSV color space, the HSB color space, the HLS color space, the HSL color space, or the like may be used.

<Calculation of Diversity of Color>

Examples of a method for calculating a diversity of color from the color information acquired by a method such as described above may include a method for calculating a variation of at least one or more elements of the color Information acquired by the above method in the region.

The method for examining the variation of at least one or more elements of the color information in the region will be described. The variation is obtained by examining the color information in the RGB color space in each pixel in a predetermined region of the image and evaluating to which extent an intensity of at least one or more color elements of red, green, and blue varies in the region. As the variation, a value obtained by dividing a variance obtained from a value of each element by an average value of the luminance of the pixel in the region may be used, or a value obtained by dividing a deviation value (standard deviation or the like) calculated therefrom by an average value of the luminance of the pixel in the region, that is, a coefficient of variation, may be used. These values may be optionally selected and used as needed.

What is important here is that the variation of the luminance thus calculated is divided by the average value of the luminance. The color of the interference fringe is dark as a whole in the region where the tear fluid layer is broken down. However, although the image is dark, the diversity of color is high due to the breakdown of the tear fluid layer. This makes it possible to specifically detect the breakdown of the tear fluid layer by dividing the variation of the luminance, such as the standard deviation, by the average value of the luminance.

<Region Subjected to Calculation of Diversity of Color in Image>

The diversity of color of the tear fluid layer interference fringe image thus obtained may be calculated using the entire image. Alternatively, the diversity of color may be calculated in a region of each grid after optionally dividing the tear fluid layer interference fringe image into a grid shape.

In a case where the entire image is used or the divided region has a large area, the calculation can be performed at a low cost, thereby making it possible to instantly analyze a plurality of the tear fluid layer interference fringe images and display numerical values.

On the other hand, when the number of the regions divided into a gild shape is increased to reduce an area of each region, the diversity of color can be evaluated in a further smaller region. In this case, the calculation cost increases with an increase in the number of the divided regions, and thus the immediacy of the analysis is vanishing.

Further, each pixel or a pixel region in which several adjacent pixels is grouped together is defined in the image and the diversity of color may be obtained in pixels surrounding each pixel or in the pixel region. The diversity of color thus obtained has further higher resolution than that in the aforementioned method in which the image is divided into a grid shape. Further, such a method is advantageous in that spatial position information is completely matched with that of the original tear fluid layer interference fringe image. On the other hand, the method requires a huge calculation cost and thus has low immediacy. Thus, the method may be preferably used for performing detailed analysis of the image or the video image which has been recorded.

Note that the original tear fluid layer interference fringe image may be appropriately magnified or reduced for calculating the diversity of color. As a magnification method, a method in which a gap of the luminance of pixel is interpolated by a function such as a bilinear method, a bicubic method, or a Lanczos method is preferable. As an effect of magnification, the state information that varies depending on each site can be acquired in more detail. On the other hand, as a method for reduction, any methods such as a nearest-neighbor method, a bilinear method, a bicubic method, and a Lanczos method may be used. As an effect of reduction, shortening of analysis time can be mentioned. These methods may be appropriately selected and used according to the need.

The diversity of color, which is obtained from the tear fluid layer interference fringe image in each grid, pixel, or region such as a pixel group, may be two-dimensionally arranged, and then stored and displayed as an image that shows the state of the tear fluid layer. For creating an image, the diversity may be expressed with a gray scale in which the luminance is increased or decreased depending on a value of the diversity. Alternatively, heat map colors obtained on the basis of a value of the diversity may be used to further facilitate the recognition of a difference. Performing such a procedure makes it possible to emphatically display a breakdown site of the tear fluid layer.

Further, the diversity of color of the tear fluid layer interference fringe image thus obtained is not only analyzed using a single image, but also analyzed in the same manner using two or more images photographed at different time or a video image to allow a temporal and spatial analysis of a degree of the breakdown of the tear fluid layer. This makes it possible to determine a portion where the tear fluid layer starts to break in the observation region or a time required for the breakdown of the tear fluid layer. Further, determining the degree of the breakdown occupied in the image and the time required for breakdown makes it possible to more accurately evaluate the severity equivalent to grade 5.

Example 1

FIG. 1 is a histogram showing distribution of luminance (red color element) in each pixel in a portion of the image (rectangular range of 320×320 pixels) determined to be grade 1, 2, 4, or 5, and the number of pixels by luminance. In grade 1, many pixels are concentrated in a low luminance range. The distribution range of the luminance of the pixels is shifted towards the higher side as the grade in the image becomes higher until grade 4. However, in grade 5, the luminance is distributed at a low value of about grade 1.

Table 1 shows an average value and a standard deviation of the luminance of the red color element in this condition, as well as a coefficient of variation (%) obtained by dividing the standard deviation by the average value. As shown in FIG. 1, the luminance average value increased in accordance with the grade level until grade 4. However, in grade 5, the luminance average value dropped to a numerical value of about grade 1. Further, similarly, the standard deviation increased in accordance with the grade level until grade 4, however, in grade 5, the standard deviation showed a numerical value similar to that of grade 4.

TABLE 1

| GRADE | LUMINANCE AVERAGE VALUE | STANDARD DEVIATION | COEFFICIENT OF VARIATION (%) |
|---|---|---|---|
| 1 | 132.0 | 8.3 | 6.3 |
| 2 | 187.6 | 17.4 | 9.3 |
| 4 | 227.3 | 23.0 | 10.1 |
| 5 | 138.6 | 22.8 | 16.3 |

From these, it can be speculated that the average value or the standard deviation of the luminance of the pixels in the region of the image, or both of them, can be used as an index for determining grades from grade 1 to 4; however, they are not suitable for determining grade 5.

As described above, the standard deviation of the image of grade 5 is approximately equal to that of the image of grade 4, that is, the image of grade 5 includes relatively many colors in the region and thus has a high level of diversity of color. On the other hand, the luminance average value in the image of grade 5 shows a low numerical value of about grade 1. This shows that, as for grade 5, the state of the tear fluid layer equivalent to grade 5 can be specifically extracted by the following formula, that is, by determining a value obtained by dividing the standard deviation of the luminance by the luminance average value, that is, the coefficient of variation of the luminance:

Coefficient of variation=Standard deviation of luminance/ Luminance average value.

In fact, as shown in Table 1, the coefficient of variation in the image of grade 5 is significantly higher than the coefficients of variation obtained in the images of other grades, meaning that this coefficient of variation can be used as a parameter for extracting the state of the tear fluid layer equivalent to grade 5.

Note that the term "state of the tear fluid layer equivalent to grade 5" described herein means a state in which the tear fluid layer is broken down, and evaluating the coefficient of variation of the luminance of the tear fluid layer interference fringe image by the method according to the present invention makes it possible to evaluate a degree of the breakdown of the tear fluid layer as well as a breakdown site in the image. That is, when the coefficient of variation becomes larger, a degree of the breakdown of the tear fluid layer can be evaluated as more significant. Further, the tear fluid layer interference fringe image is obtained by photographing the cornea. Thus, for example, dividing the tear fluid layer interference fringe image into a predetermined division and determining the coefficient of variation in each division using the aforementioned method makes it possible to grasp the breakdown of the tear fluid layer at a position on the cornea corresponding to the division.

FIG. 2 is a schematic diagram illustrating a result of evaluating a degree of the breakdown of the tear fluid layer and a location of the breakdown on the cornea in each of images of grade 1, 2, 4, and 5 using the aforementioned method. Only small portions of the images of grade 1 to grade 4 sometimes showed a spot-like tear fluid layer state equivalent to grade 5, that is, a state in which the tear fluid layer is broken down. However, such a state was not observed over the entire image. On the other hand, when the image equivalent to grade 5 was evaluated, the breakdown of the tear fluid layer was widely observed over the entire image immediately after blinking. Thus, a relation between the coefficient of variation of the luminance and a region area thereof in the tear fluid layer interference fringe image can be used as an index for more accurately determining grade 5. For example, the tear fluid layer is determined to be broken down if the coefficient of variation exceeds a threshold value, and grade 5 is determined if a region area occupied by the coefficient of variation indicating the breakdown of the tear fluid layer exceeds a predetermined threshold value. A method with such determination makes it possible to accurately and automatically evaluate grade 5.

This means that a time from immediately after blinking to the breakdown of the tear fluid layer (NIBUT) can be automatically acquired. FIG. 3 is a schematic diagram illustrating a method for automatically calculating the time until the breakdown of the tear fluid layer (NIBUT). Apart from an example showing a particularly severe dry eye symptom such as seen in grade 5, in many cases, the cornea and the conjunctiva are covered by the tear fluid layer immediately after blinking. However, if there is not enough amount of oil layers, fluid layers, membrane-bound mucins expressed on the cornea and the conjunctiva, or the like, the breakdown of the tear fluid layer begins to occur a while after blinking. NIBUT can be obtained by the following formula where $t_0$ represents a time immediately after blinking and to represents a time when the breakdown of the tear fluid layer is detected using the coefficient of variation of color of the interference fringe of the present invention or a numerical value equivalent thereto.

$$NIBUT = T_1 - t_0$$

Of these times, $t_0$ can be obtained as a time when a physical quantity (e.g., luminance) changes from a value lower than a threshold value to a value of a threshold value or higher at a site of interest composed of a region having one or more pixels in the tear fluid layer interference fringe image. As this physical quantity, the luminance of the tear fluid layer interference fringe image or a standard deviation of the luminance may be used. On the other hand, $t_1$ may be determined, for example, by sequentially analyzing two or more (frames) of the tear fluid layer interference fringe images arranged successively as a moving image by the aforementioned method and using an index indicating whether a region area of the coefficient of variation which exceeds a certain value, that is, a region area of the tear fluid layer which is broken down, exceeds a certain value.

While the present invention has been described above, it is to be understood that the present invention is not limited to the above-described examples and may be modified and embodied in various aspects. In the aforementioned description, the tear fluid layer interference fringe image acquiring device and the dynamics evaluation device of a tear fluid layer are described as a separate hardware. However, the tear fluid layer interference fringe image acquiring device and the dynamics evaluation device of a tear fluid layer may be configured as an integrated hardware, and the processing unit, the storing unit, and the like, for information processing, may be provided in each of the tear fluid layer interference fringe image acquiring device and the dynamics evaluation device of a tear fluid layer or partially shared by these devices. The dynamics evaluation device of a tear fluid layer is only required to have a configuration capable of performing the processing described above to the tear fluid layer interference fringe image. Note that, in the present examples, the image of grade 3 is not validated. However, the image of grade 3 has characteristics (luminance average value, standard deviation, and coefficient of variation) between the image of grade 2 and the image of grade 4, and thus the image of grade 3 is never be erroneously determined as grade 5 by the method of the present examples. Further, the grade 5 can be automatically determined by the present invention, and the image determined not to be grade 5 can be automatically determined to be grades 1 to 4 by the method described in Patent Literature 3. Thus, grades 1 to 5 can be automatically determined by combining the method in Patent Literature 3 and the method of the present invention.

INDUSTRIAL APPLICABILITY

The present invention can be used as a method for objectively digitalizing the state of a tear fluid layer that breaks down in the diagnosis of dry eye using the interference fringe image of the tear fluid layer without relying on the ability of the observer. In particular, in determining a patient having an extremely severe dry eye, for example, in Sjögren's syndrome, which is classified as grade 5 by conventional visual inspection, the present invention makes it possible not only to automatically evaluate grade 5 by determining the breakdown of the tear fluid layer in a large portion of the image immediately after blinking through a dynamic analysis of a temporal and spatial transition of the breakdown of the tear fluid layer, but also to envisage a more appropriate diagnosis and a treatment adapted to a symptom by performing detailed evaluation using the time until the breakdown of the tear fluid layer and the like.

The invention claimed is:

1. A method for evaluating dynamics of a tear fluid layer, comprising:
   a step of acquiring color information of each pixel in a predetermined region of a tear fluid layer interference fringe image, which is a moving image or a plurality of static images;
   a step of calculating a numerical value indicating a diversity of color from the acquired color information;
   a step of calculating an average value of the color information; and
   a step of calculating a coefficient of variation on a basis of the numerical value indicating the diversity of color and the average value of the color information, wherein:
   the coefficient of variation is used as an index for evaluating the dynamics of the tear fluid layer,
   the color information is luminance or brightness of the pixel, and
   the numerical value indicating the diversity of color is a standard deviation of the luminance or the brightness.

2. The method for evaluating dynamics of a tear fluid layer according to claim 1, wherein the coefficient of variation is a numerical value obtained by dividing a numerical value indicating a diversity of the color by the average value of the color information.

3. The method for evaluating dynamics of a tear fluid layer according to claim 1, comprising:
   a step of calculating a region area of a region indicated by the coefficient of variation exceeding a threshold value; and a determination step of determining whether the region area exceeds a threshold value.

4. The method for evaluating dynamics of a tear fluid layer according to claim 3, comprising:
a step of acquiring a predetermined start time;
a step of acquiring a time when the region area exceeds the threshold value the determination step as an end time; and
a step of calculating a time from the start time to the end time.

5. The method for evaluating dynamics of a tear fluid layer according to claim 1, wherein the coefficient of variation is used as an index for evaluating grade 5 in severity of dry eye.

6. The method for evaluating dynamics of a tear fluid layer according to claim 1, wherein the numerical value indicating the diversity of color or the coefficient of variation is used as an index for evaluating grades 1 to 4 in the severity of dry eye.

7. A device for evaluating dynamics of a tear fluid layer, comprising:
a processing unit; and
a storing unit configured to store a tear fluid layer interference fringe image, which is a moving image or a plurality of static images, wherein the processing unit is configured to:
acquire color information of each pixel in a predetermined region of a tear fluid layer interference fringe image;
calculate a numerical value indicating a diversity of color from the acquired color information;
calculate an average value of the color information; and
calculate a coefficient of variation on a basis of the numerical value indicating the diversity of color and the average value of the color information, wherein:
the coefficient of variation is used as an index for evaluating the dynamics of the tear fluid layer,
the color information is luminance or brightness of the pixel, and
the numerical value indicating the diversity of color is a standard deviation of the luminance or the brightness.

8. A method for evaluating dynamics of a tear fluid layer, comprising:
a step of acquiring color information of each pixel in a predetermined region of a tear fluid layer interference fringe image, which is a moving image or a plurality of static images;
a step of calculating a numerical value indicating a diversity of color from the acquired color information;
a step of calculating an average value of the color information; and
a step of calculating a coefficient of variation on a basis of the numerical value indicating the diversity of color and the average value of the color information, wherein:
the coefficient of variation is used as an index for evaluating the dynamics of the tear fluid layer, and
the coefficient of variation is a numerical value obtained by dividing the numerical value indicating the diversity of the color by the average value of the color information.

9. The method for evaluating dynamics of a tear fluid layer according to claim 8, wherein:
the color information is luminance or brightness of the pixel, and
the numerical value indicating the diversity of color is a variation of the luminance or the brightness.

10. The method for evaluating dynamics of a tear fluid layer according to claim 8, comprising:
a step of calculating a region area of a region indicated by the coefficient of variation exceeding a threshold value; and
a determination step of determining whether the region area exceeds a threshold value.

11. The method for evaluating dynamics of a tear fluid layer according to claim 10, comprising:
a step of acquiring a predetermined start time;
a step of acquiring a time when the region area exceeds the threshold value by the determination step as an end time; and
a step of calculating a time from the start time to the end time.

12. The method for evaluating dynamics of a tear fluid layer according to claim 8, wherein the coefficient of variation is used as an index for evaluating grade 5 in severity of dry eye.

13. The method for evaluating dynamics of a tear fluid layer according to claim 8, wherein the numerical value indicating the diversity of color or the coefficient of variation is used as an index for evaluating grades 1 to 4 in the severity of dry eye.

14. A device for evaluating dynamics of a tear fluid layer, comprising:
a processing unit; and
a storing unit configured to store a tear fluid layer interference fringe image, which is a moving image or a plurality of static images, wherein the processing unit is configured to:
acquire color information of each pixel in a predetermined region of the tear fluid layer interference fringe image;
calculate a numerical value indicating a diversity of color from the acquired color information;
calculate an average value of the color information; and
calculate a coefficient of variation on a basis of the numerical value indicating the diversity of color and the average value of the color information, wherein:
the coefficient of variation is used as an index for evaluating the dynamics of the tear fluid layer, and
the coefficient of variation is a numerical value obtained by dividing the numerical value indicating the diversity of the color by the average value of the color information.

* * * * *